United States Patent
Corrigan

(10) Patent No.: US 9,757,520 B2
(45) Date of Patent: Sep. 12, 2017

(54) INJECTION DEVICE

(75) Inventor: Joseph Peter Corrigan, Cambridge (GB)

(73) Assignee: Cilag gmBh International, Landis & Gystrasse 1 (CH)

( * ) Notice: Subject to any disclaimer, the term of this patent is extended or adjusted under 35 U.S.C. 154(b) by 783 days.

(21) Appl. No.: 12/301,478

(22) PCT Filed: May 30, 2007

(86) PCT No.: PCT/GB2007/001999
§ 371 (c)(1),
(2), (4) Date: Oct. 8, 2009

(87) PCT Pub. No.: WO2007/138317
PCT Pub. Date: Dec. 6, 2007

(65) Prior Publication Data
US 2010/0016794 A1 Jan. 21, 2010

(30) Foreign Application Priority Data
Jun. 1, 2006 (GB) .................................. 0610856.7

(51) Int. Cl.
*A61M 5/20* (2006.01)
*A61M 5/32* (2006.01)

(52) U.S. Cl.
CPC ......... *A61M 5/2033* (2013.01); *A61M 5/3202* (2013.01); *A61M 5/3204* (2013.01);
(Continued)

(58) Field of Classification Search
CPC .... A61M 2005/2013; A61M 2005/206; A61M 2005/208; A61M 5/2033; A61M 5/3202;
(Continued)

(56) References Cited

U.S. PATENT DOCUMENTS

| 1,845,036 A | 2/1932 | Busher |
| 2,019,382 A | 10/1935 | Aronson |
| (Continued) | | |

FOREIGN PATENT DOCUMENTS

| CA | 2445511 A1 | 11/2002 |
| CH | 518102 A | 1/1972 |
| (Continued) | | |

OTHER PUBLICATIONS

International Search Report dated Sep. 5, 2005; International Application No. PCT/GB2005/002117.
(Continued)

*Primary Examiner* — Nathan R Price
*Assistant Examiner* — Weng Lee

(57) ABSTRACT

An injection device 110 is described having a housing 112 that receives a syringe 114 having a needle 118, wherein the syringe is supported in a syringe carrier 150. The syringe 114 and syringe carrier 150 are biased by a return spring 126 from an extended position in which the needle 118 extends from the housing 112 through an exit aperture 128 to a retracted position in which it does not. A drive spring 130 acts via a drive to advance the syringe 114 from its retracted position to its extended position and discharge its contents through the needle 118 and a return spring 126, brought into play when the drive has reached a nominal return position, restores the syringe 114 to its retracted position. The syringe carrier 150 is designed to restrict rearward movement of the syringe so that the injection device is less prone to failure and damage to is components than prior art devices.

4 Claims, 4 Drawing Sheets

(52) U.S. Cl.
CPC ....... *A61M 5/326* (2013.01); *A61M 2005/206* (2013.01); *A61M 2005/208* (2013.01); *A61M 2005/2013* (2013.01)

(58) Field of Classification Search
CPC ................ A61M 5/3204; A61M 5/326; A61M 2005/2086; A61M 55/2033
USPC ... 604/218, 225, 157, 156, 36, 38, 232–242, 604/131–149, 181–188, 192–198
See application file for complete search history.

(56) References Cited

U.S. PATENT DOCUMENTS

| | | |
|---|---|---|
| 2,147,616 A | 2/1939 | Chaput |
| 2,295,849 A | 9/1942 | Kayden |
| 2,531,267 A | 11/1950 | Harisch |
| 2,764,977 A | 10/1956 | Ferguson |
| 2,828,742 A | 4/1958 | Ashkenaz |
| 2,854,975 A | 10/1958 | Cohen |
| 3,076,455 A | 2/1963 | McConnaughey et al. |
| 3,131,692 A | 5/1964 | Love |
| 3,320,955 A | 5/1967 | Sarnoff |
| 3,329,146 A | 7/1967 | Waldman |
| 3,543,603 A | 12/1970 | Gley |
| 3,656,472 A | 4/1972 | Moura |
| 3,702,608 A * | 11/1972 | Tibbs .......................... 604/136 |
| 3,742,948 A | 7/1973 | Post et al. |
| 3,797,488 A | 3/1974 | Hurschman et al. |
| 3,797,489 A | 3/1974 | Sarnoff |
| 3,880,163 A | 4/1975 | Ritterskamp |
| 3,976,069 A | 8/1976 | Ong |
| 4,165,739 A | 8/1979 | Doherty et al. |
| 4,180,070 A | 12/1979 | Genese |
| 4,185,628 A | 1/1980 | Kopfer |
| 4,194,505 A | 3/1980 | Schmitz |
| 4,222,380 A | 9/1980 | Terayama |
| 4,231,368 A | 11/1980 | Becker |
| 4,236,516 A | 12/1980 | Nilson |
| 4,237,882 A | 12/1980 | Wickham |
| 4,299,238 A | 11/1981 | Baidwan et al. |
| 4,333,459 A | 6/1982 | Becker |
| 4,378,015 A | 3/1983 | Wardlaw |
| 4,394,863 A | 7/1983 | Bartner |
| 4,403,989 A | 9/1983 | Christensen et al. |
| 4,407,283 A | 10/1983 | Reynolds |
| 4,425,120 A | 1/1984 | Sampson et al. |
| 4,430,082 A | 2/1984 | Schwabacher |
| 4,521,237 A | 6/1985 | Logothetis |
| 4,561,856 A | 12/1985 | Cochran et al. |
| 4,627,835 A | 12/1986 | Fenton, Jr. |
| 4,636,201 A | 1/1987 | Ambrose et al. |
| 4,639,250 A | 1/1987 | Rycroft |
| 4,642,099 A | 2/1987 | Phillips et al. |
| 4,676,530 A | 6/1987 | Nordgren et al. |
| 4,717,383 A | 1/1988 | Phillips et al. |
| 4,744,786 A | 5/1988 | Hooven et al. |
| 4,787,891 A | 11/1988 | Levin et al. |
| 4,874,383 A | 10/1989 | McNaughton |
| 4,874,384 A | 10/1989 | Nunez |
| 4,929,232 A | 5/1990 | Sweeney et al. |
| 4,969,870 A | 11/1990 | Kramer et al. |
| 4,988,339 A | 1/1991 | Vadher |
| 4,994,034 A | 2/1991 | Botich et al. |
| 5,009,646 A | 4/1991 | Sudo et al. |
| 5,026,349 A | 6/1991 | Schmitz et al. |
| 5,057,079 A | 10/1991 | Tiemann et al. |
| 5,092,842 A | 3/1992 | Bechtold et al. |
| 5,098,400 A | 3/1992 | Crouse et al. |
| 5,112,119 A | 5/1992 | Cooke et al. |
| 5,114,406 A | 5/1992 | Gabriel et al. |
| 5,122,119 A | 6/1992 | Lucas |
| 5,137,516 A | 8/1992 | Rand et al. |
| 5,141,496 A | 8/1992 | Dalto et al. |
| 5,147,325 A | 9/1992 | Mitchell et al. |
| 5,156,599 A | 10/1992 | Ranford et al. |
| 5,176,643 A | 1/1993 | Kramer et al. |
| 5,190,526 A | 3/1993 | Murray et al. |
| 5,242,416 A | 9/1993 | Hutson |
| 5,250,026 A | 10/1993 | Ehrlich et al. |
| 5,250,037 A | 10/1993 | Bitdinger |
| 5,263,933 A | 11/1993 | Novacek et al. |
| 5,267,963 A | 12/1993 | Bachynsky |
| 5,271,744 A | 12/1993 | Kramer et al. |
| 5,295,965 A | 3/1994 | Wilmot |
| 5,300,030 A | 4/1994 | Crossman et al. |
| 5,312,364 A | 5/1994 | Jacobs |
| 5,330,081 A | 7/1994 | Davenport |
| 5,330,430 A | 7/1994 | Sullivan |
| 5,356,395 A | 10/1994 | Chen |
| 5,358,489 A | 10/1994 | Wyrick |
| 5,364,369 A | 11/1994 | Reynolds |
| 5,368,577 A | 11/1994 | Teoh et al. |
| 5,372,586 A | 12/1994 | Haber et al. |
| 5,391,151 A | 2/1995 | Wilmot |
| 5,405,362 A | 4/1995 | Kramer et al. |
| 5,411,488 A | 5/1995 | Pagay et al. |
| 5,425,715 A | 6/1995 | Dalling et al. |
| 5,451,210 A | 9/1995 | Kramer et al. |
| 5,478,316 A | 12/1995 | Bitdinger et al. |
| 5,480,387 A | 1/1996 | Gabriel et al. |
| 5,487,732 A | 1/1996 | Jeffrey |
| 5,489,256 A | 2/1996 | Adair |
| 5,503,627 A | 4/1996 | McKinnon et al. |
| 5,514,097 A | 5/1996 | Knauer |
| 5,520,653 A | 5/1996 | Reilly et al. |
| 5,540,660 A | 7/1996 | Jenson et al. |
| 5,540,666 A | 7/1996 | Barta et al. |
| 5,540,709 A | 7/1996 | Ramel et al. |
| 5,567,160 A | 10/1996 | Massino |
| 5,569,191 A | 10/1996 | Meyer |
| 5,569,192 A | 10/1996 | van der Wal |
| 5,575,777 A | 11/1996 | Cover et al. |
| 5,599,302 A | 2/1997 | Lilley et al. |
| 5,599,309 A | 2/1997 | Marshall et al. |
| 5,607,395 A | 3/1997 | Ragsdale et al. |
| 5,609,577 A | 3/1997 | Haber et al. |
| 5,609,584 A | 3/1997 | Gettig et al. |
| 5,611,785 A | 3/1997 | Mito et al. |
| 5,637,094 A | 6/1997 | Stewart, Jr. et al. |
| 5,645,536 A | 7/1997 | Whisson |
| 5,647,845 A | 7/1997 | Haber et al. |
| 5,649,912 A | 7/1997 | Peterson |
| 5,658,259 A | 8/1997 | Pearson et al. |
| 5,665,071 A | 9/1997 | Wyrick |
| 5,681,291 A | 10/1997 | Galli |
| 5,697,908 A | 12/1997 | Imbert |
| 5,702,367 A | 12/1997 | Cover et al. |
| 5,704,911 A | 1/1998 | Parsons et al. |
| 5,709,662 A | 1/1998 | Olive et al. |
| 5,713,866 A | 2/1998 | Wilmot |
| 5,748,316 A | 5/1998 | Wakabayashi et al. |
| 5,779,668 A | 7/1998 | Grabenkort |
| 5,779,677 A | 7/1998 | Frezza |
| 5,807,334 A | 9/1998 | Hodosh et al. |
| 5,817,058 A | 10/1998 | Shaw |
| 5,827,262 A | 10/1998 | Neftel et al. |
| 5,843,036 A | 12/1998 | Olive et al. |
| 5,855,839 A | 1/1999 | Brunel |
| 5,865,795 A | 2/1999 | Schiff et al. |
| 5,865,804 A | 2/1999 | Bachynsky |
| 5,868,711 A | 2/1999 | Kramer et al. |
| 5,879,327 A | 3/1999 | Moreau DeFarges et al. |
| 5,913,843 A | 6/1999 | Jentzen |
| 5,928,205 A | 7/1999 | Marshall |
| 5,954,738 A | 9/1999 | LeVaughn et al. |
| 5,957,897 A | 9/1999 | Jeffrey |
| 5,960,797 A | 10/1999 | Kramer et al. |
| 5,997,513 A | 12/1999 | Smith et al. |
| 6,007,515 A | 12/1999 | Epstein et al. |
| 6,015,438 A | 1/2000 | Shaw |
| 6,017,330 A | 1/2000 | Hitchins et al. |
| 6,036,675 A | 3/2000 | Thorne et al. |
| 6,045,534 A | 4/2000 | Jacobsen et al. |
| 6,068,614 A | 5/2000 | Kimber et al. |

(56) References Cited

U.S. PATENT DOCUMENTS

| | | | |
|---|---|---|---|
| 6,077,247 | A | 6/2000 | Marshall et al. |
| 6,083,197 | A | 7/2000 | Umbaugh |
| 6,086,562 | A | 7/2000 | Jacobsen et al. |
| 6,090,070 | A | 7/2000 | Hager et al. |
| 6,090,078 | A | 7/2000 | Erskine |
| 6,090,897 | A | 7/2000 | Akasaki et al. |
| 6,099,503 | A | 8/2000 | Stradella |
| 6,099,504 | A | 8/2000 | Gross |
| 6,123,684 | A | 9/2000 | Deboer et al. |
| 6,139,534 | A | 10/2000 | Niedospial, Jr. et al. |
| 6,159,161 | A | 12/2000 | Hodosh |
| 6,159,181 | A | 12/2000 | Crossman et al. |
| 6,159,184 | A | 12/2000 | Perez et al. |
| 6,162,199 | A | 12/2000 | Geringer |
| 6,171,276 | B1 | 1/2001 | Adam et al. |
| 6,179,812 | B1 | 1/2001 | Botich et al. |
| 6,186,980 | B1 | 2/2001 | Brunel |
| 6,190,363 | B1 | 2/2001 | Gabbard et al. |
| 6,193,696 | B1 | 2/2001 | Jansen et al. |
| 6,203,530 | B1 | 3/2001 | Stewart, Sr. |
| 6,209,738 | B1 | 4/2001 | Jansen et al. |
| 6,221,044 | B1 | 4/2001 | Grecco |
| 6,228,055 | B1 | 5/2001 | Foerster et al. |
| 6,258,068 | B1 | 7/2001 | Kirchhofer et al. |
| 6,270,479 | B1 * | 8/2001 | Bergens et al. ............... 604/156 |
| 6,280,421 | B1 | 8/2001 | Kirchhofer et al. |
| 6,290,683 | B1 | 9/2001 | Erez et al. |
| 6,293,925 | B1 | 9/2001 | Safabash et al. |
| RE37,439 | E | 11/2001 | Firth et al. |
| 6,317,939 | B1 | 11/2001 | Malin |
| 6,330,960 | B1 | 12/2001 | Faughey et al. |
| 6,332,875 | B2 | 12/2001 | Inkpen et al. |
| 6,371,939 | B2 | 4/2002 | Bergens et al. |
| 6,371,959 | B1 | 4/2002 | Trice |
| 6,387,078 | B1 | 5/2002 | Gillespie, III |
| 6,391,003 | B1 | 5/2002 | Lesch, Jr. |
| 6,419,658 | B1 | 7/2002 | Restelli et al. |
| 6,428,528 | B2 | 8/2002 | Sadowski et al. |
| 6,447,480 | B1 | 9/2002 | Brunel |
| 6,454,743 | B1 | 9/2002 | Weber |
| 6,454,746 | B1 | 9/2002 | Bydlon et al. |
| 6,461,333 | B1 | 10/2002 | Frezza |
| 6,491,667 | B1 | 12/2002 | Keane et al. |
| 6,517,517 | B1 | 2/2003 | Farrugia et al. |
| 6,537,252 | B1 | 3/2003 | Hansen |
| 6,544,234 | B1 * | 4/2003 | Gabriel ........................ 604/207 |
| 6,565,540 | B1 | 5/2003 | Perouse et al. |
| 6,565,553 | B2 | 5/2003 | Sadowski et al. |
| 6,569,115 | B1 | 5/2003 | Barker et al. |
| 6,569,123 | B2 | 5/2003 | Alchas et al. |
| 6,569,124 | B1 | 5/2003 | Perouse |
| 6,572,581 | B1 | 6/2003 | Landua |
| 6,575,939 | B1 | 6/2003 | Brunel |
| 6,585,702 | B1 | 7/2003 | Brunel |
| 6,589,210 | B1 * | 7/2003 | Rolfe ................... A61M 5/2033 604/136 |
| 6,595,957 | B1 | 7/2003 | Griffiths et al. |
| 6,595,962 | B1 | 7/2003 | Perthu |
| 6,599,272 | B1 | 7/2003 | Hjertman et al. |
| 6,607,508 | B2 | 8/2003 | Knauer |
| 6,607,510 | B2 | 8/2003 | Landau |
| 6,613,022 | B1 | 9/2003 | Doyle |
| 6,620,137 | B2 | 9/2003 | Kirchhofer et al. |
| 6,638,256 | B2 | 10/2003 | Jansen et al. |
| 6,641,554 | B1 | 11/2003 | Landau |
| 6,641,560 | B1 | 11/2003 | Bechtold et al. |
| 6,641,565 | B1 | 11/2003 | Lavi et al. |
| 6,645,170 | B2 | 11/2003 | Landua |
| 6,645,181 | B1 | 11/2003 | Lavi et al. |
| 6,648,835 | B1 | 11/2003 | Shemesh |
| 6,648,850 | B2 | 11/2003 | Landau |
| 6,656,163 | B1 | 12/2003 | Marshall et al. |
| 6,673,049 | B2 | 1/2004 | Hommann et al. |
| 6,676,630 | B2 | 1/2004 | Landau et al. |
| 6,689,093 | B2 | 2/2004 | Landau et al. |
| 6,692,469 | B1 | 2/2004 | Weekes et al. |
| 6,699,220 | B2 | 3/2004 | Rolfe |
| 6,740,062 | B2 | 5/2004 | Hjertman |
| 6,743,199 | B2 | 6/2004 | Shue et al. |
| 6,743,203 | B1 | 6/2004 | Pickhard et al. |
| 6,746,429 | B2 | 6/2004 | Sadowski et al. |
| 6,746,438 | B1 | 6/2004 | Arnissolle |
| 6,767,336 | B1 | 7/2004 | Kaplan |
| 6,770,056 | B2 | 8/2004 | Price et al. |
| 6,776,777 | B2 | 8/2004 | Barrelle |
| 6,783,509 | B1 | 8/2004 | Landau et al. |
| 6,793,161 | B1 | 9/2004 | Fujia et al. |
| 6,796,967 | B2 | 9/2004 | Jensen |
| 6,811,548 | B2 | 11/2004 | Jeffrey |
| 6,817,987 | B2 | 11/2004 | Vetter et al. |
| 6,846,303 | B2 | 1/2005 | Eakins et al. |
| 6,875,205 | B2 | 4/2005 | Leinsing |
| 6,890,319 | B1 | 5/2005 | Crocker |
| 6,899,698 | B2 | 5/2005 | Sams |
| 6,902,543 | B1 | 6/2005 | Cherif-Cheikh et al. |
| 6,932,793 | B1 | 8/2005 | Marshall et al. |
| 6,939,319 | B1 | 9/2005 | Anstead et al. |
| 6,939,330 | B1 | 9/2005 | McConnell et al. |
| 6,979,316 | B1 | 12/2005 | Rubin et al. |
| 7,066,907 | B2 | 6/2006 | Crossman et al. |
| 7,097,071 | B2 | 8/2006 | Anderson et al. |
| 7,097,634 | B2 | 8/2006 | Gilbert |
| 7,118,553 | B2 | 10/2006 | Scherer |
| 7,156,823 | B2 | 1/2007 | Landau et al. |
| 7,160,913 | B2 | 1/2007 | Schneider |
| 7,294,122 | B2 | 11/2007 | Kubo et al. |
| 7,354,427 | B2 | 4/2008 | Fangrow |
| RE40,428 | E | 7/2008 | Keane et al. |
| 7,442,185 | B2 | 10/2008 | Amark et al. |
| 7,465,289 | B2 * | 12/2008 | Marshall ........................ 604/136 |
| 7,470,258 | B2 | 12/2008 | Barker et al. |
| 7,507,227 | B2 | 3/2009 | Fangrow |
| 7,510,547 | B2 | 3/2009 | Fangrow |
| 7,510,548 | B2 | 3/2009 | Fangrow |
| 7,513,895 | B2 | 4/2009 | Fangrow |
| 7,534,238 | B2 | 5/2009 | Fangrow |
| 7,547,300 | B2 | 6/2009 | Fangrow |
| 7,569,043 | B2 | 8/2009 | Fangrow |
| 7,618,396 | B2 | 11/2009 | Slate et al. |
| 7,635,356 | B2 | 12/2009 | Stamp |
| 7,645,271 | B2 | 1/2010 | Fangrow |
| 7,654,995 | B2 | 2/2010 | Warren et al. |
| 7,658,733 | B2 | 2/2010 | Fangrow |
| 7,678,333 | B2 | 3/2010 | Reynolds et al. |
| 7,682,345 | B2 | 3/2010 | Savage |
| 7,717,879 | B2 | 5/2010 | Mansouri |
| 7,744,561 | B2 | 6/2010 | Stamp |
| 7,759,654 | B2 | 7/2010 | Yan et al. |
| 7,794,434 | B2 | 9/2010 | Mounce et al. |
| 7,799,009 | B2 | 9/2010 | Niedospial, Jr. et al. |
| 7,811,262 | B2 | 10/2010 | Moberg et al. |
| 7,828,764 | B2 | 11/2010 | Moberg et al. |
| 7,871,397 | B2 | 1/2011 | Schraga |
| 7,879,010 | B2 | 2/2011 | Hunn et al. |
| 7,883,499 | B2 | 2/2011 | Fangrow |
| 7,959,715 | B2 | 6/2011 | Kavazov et al. |
| 7,972,321 | B2 | 7/2011 | Fangrow |
| 7,976,499 | B2 | 7/2011 | Grunhut et al. |
| 8,100,154 | B2 | 1/2012 | Reynolds et al. |
| 8,177,768 | B2 | 5/2012 | Leinsing |
| 8,277,414 | B2 | 10/2012 | Barrow-Williams et al. |
| 8,313,463 | B2 | 11/2012 | Barrow-Williams et al. |
| 8,409,138 | B2 | 4/2013 | James et al. |
| 8,409,141 | B2 | 4/2013 | Johansen et al. |
| 8,491,530 | B2 | 7/2013 | Maritan |
| 8,696,628 | B2 | 4/2014 | Grunhut |
| 8,932,264 | B2 | 1/2015 | DeSalvo |
| 9,314,574 | B2 | 4/2016 | Roberts et al. |
| 2001/0005781 | A1 * | 6/2001 | Bergens ............... A61M 5/2033 604/208 |
| 2001/0037087 | A1 | 11/2001 | Knauer |
| 2001/0037089 | A1 | 11/2001 | Domici, Jr. |
| 2001/0049496 | A1 | 12/2001 | Kirchhofer et al. |
| 2001/0051789 | A1 | 12/2001 | Parsons |

(56) References Cited

U.S. PATENT DOCUMENTS

| | | |
|---|---|---|
| 2002/0032412 A1 | 3/2002 | Riemelmoser |
| 2002/0072709 A1 | 6/2002 | Sadowski et al. |
| 2002/0095120 A1 | 7/2002 | Larsen et al. |
| 2002/0151839 A1 | 10/2002 | Landau |
| 2002/0161334 A1 | 10/2002 | Castellano et al. |
| 2002/0165500 A1 | 11/2002 | Bechtold et al. |
| 2002/0173752 A1 | 11/2002 | Polzin |
| 2002/0183690 A1 | 12/2002 | Arnisolle |
| 2003/0036679 A1 | 2/2003 | Kortenbach |
| 2003/0036725 A1 | 2/2003 | Lavi et al. |
| 2003/0050609 A1 | 3/2003 | Sams |
| 2003/0060773 A1 | 3/2003 | Nguyen |
| 2003/0065286 A1 | 4/2003 | Landau |
| 2003/0078546 A1 | 4/2003 | Jensen |
| 2003/0088207 A1 | 5/2003 | Rogatchev et al. |
| 2003/0088216 A1 | 5/2003 | Py |
| 2003/0093030 A1 | 5/2003 | Landau |
| 2003/0093035 A1 | 5/2003 | Mohammed |
| 2003/0093036 A1 | 5/2003 | Crossman et al. |
| 2003/0105430 A1 | 6/2003 | Lavi et al. |
| 2003/0109833 A1 | 6/2003 | Sahpe |
| 2003/0120212 A1 | 6/2003 | Dedig et al. |
| 2003/0120222 A1 | 6/2003 | Vaillancourt |
| 2003/0121815 A1 | 7/2003 | Bergeron et al. |
| 2003/0135157 A1 | 7/2003 | Saulenas et al. |
| 2003/0181859 A1 | 9/2003 | Brunel |
| 2003/0184973 A1 | 10/2003 | Nagata et al. |
| 2003/0196928 A1 | 10/2003 | Parsons |
| 2003/0199814 A1 | 10/2003 | Parsons et al. |
| 2003/0208164 A1 | 11/2003 | Botich et al. |
| 2003/0212362 A1 | 11/2003 | Roser |
| 2003/0212370 A1 | 11/2003 | Barrelle |
| 2003/0212380 A1 | 11/2003 | Barrelle |
| 2003/0225368 A1 | 12/2003 | Landau et al. |
| 2003/0229308 A1 | 12/2003 | Tsals et al. |
| 2003/0233070 A1 | 12/2003 | De La Serna et al. |
| 2003/0236502 A1 | 12/2003 | De La Serna et al. |
| 2003/0236504 A1 | 12/2003 | Chen |
| 2004/0002684 A1 | 1/2004 | Lopez |
| 2004/0015134 A1 | 1/2004 | Lavi et al. |
| 2004/0019326 A1 | 1/2004 | Gilbert et al. |
| 2004/0024367 A1 | 2/2004 | Gilbert |
| 2004/0039336 A1 | 2/2004 | Amark et al. |
| 2004/0039366 A1 | 2/2004 | MacLeod |
| 2004/0069044 A1 | 4/2004 | Lavi et al. |
| 2004/0087897 A1 | 5/2004 | Hjertman |
| 2004/0094396 A1 | 5/2004 | Lee et al. |
| 2004/0102740 A1 | 5/2004 | Meloul |
| 2004/0111054 A1 | 6/2004 | Landau et al. |
| 2004/0111057 A1 | 6/2004 | Wilkinson |
| 2004/0133159 A1 | 7/2004 | Haider et al. |
| 2004/0138618 A1 | 7/2004 | Mazzoni |
| 2004/0143224 A1 | 7/2004 | Field et al. |
| 2004/0153033 A1 | 8/2004 | Mazzoni |
| 2004/0225262 A1 | 11/2004 | Fathallah et al. |
| 2004/0243065 A1 | 12/2004 | McConnell et al. |
| 2005/0011780 A1 | 1/2005 | Simon et al. |
| 2005/0020979 A1 | 1/2005 | Westbye et al. |
| 2005/0020980 A1 | 1/2005 | Inoue et al. |
| 2005/0027255 A1 | 2/2005 | Lavi et al. |
| 2005/0033234 A1 | 2/2005 | Sadowski et al. |
| 2005/0035029 A1 | 2/2005 | Grob |
| 2005/0040716 A1 | 2/2005 | Schmid et al. |
| 2005/0049550 A1 | 3/2005 | Kirchhofer et al. |
| 2005/0049561 A1 | 3/2005 | Hommann et al. |
| 2005/0075608 A1 | 4/2005 | Holdgate et al. |
| 2005/0085776 A1 | 4/2005 | Hommann et al. |
| 2005/0090782 A1 | 4/2005 | Marshall et al. |
| 2005/0097238 A1 | 5/2005 | Oomori et al. |
| 2005/0101919 A1 | 5/2005 | Brunnberg |
| 2005/0113747 A1 | 5/2005 | Moir |
| 2005/0124940 A1 | 6/2005 | Martin et al. |
| 2005/0125019 A1 | 6/2005 | Kudna et al. |
| 2005/0137523 A1 | 6/2005 | Wyatt et al. |
| 2005/0168855 A1 | 8/2005 | Fanelli et al. |
| 2005/0203466 A1 | 9/2005 | Hommann et al. |
| 2005/0209554 A1 | 9/2005 | Landau |
| 2005/0215941 A1 | 9/2005 | Bernard et al. |
| 2005/0215951 A1 | 9/2005 | Saulenas et al. |
| 2005/0222539 A1 | 10/2005 | Gonzales et al. |
| 2005/0261633 A1 | 11/2005 | Khalaj |
| 2005/0261634 A1 | 11/2005 | Karlsson |
| 2005/0267403 A1 | 12/2005 | Landau et al. |
| 2005/0273054 A1 | 12/2005 | Asch |
| 2005/0273055 A1 | 12/2005 | Harrison et al. |
| 2005/0277885 A1 | 12/2005 | Scherer |
| 2005/0277886 A1 | 12/2005 | Hommann et al. |
| 2005/0277896 A1 | 12/2005 | Messerli et al. |
| 2005/0288633 A1 | 12/2005 | Jeffrey |
| 2006/0016835 A1 | 1/2006 | Perry |
| 2006/0030819 A1 | 2/2006 | Young et al. |
| 2006/0036216 A1 | 2/2006 | Rimlinger et al. |
| 2006/0036217 A1 | 2/2006 | Doyle |
| 2006/0069345 A1 | 3/2006 | Anderson et al. |
| 2006/0069348 A1 | 3/2006 | Parker et al. |
| 2006/0069350 A1 | 3/2006 | Buenger et al. |
| 2006/0079834 A1 | 4/2006 | Tennican et al. |
| 2006/0100588 A1 | 5/2006 | Brunnberg et al. |
| 2006/0106295 A1 | 5/2006 | Jais et al. |
| 2006/0161111 A1 | 7/2006 | Potter et al. |
| 2006/0178630 A1 | 8/2006 | Bostrom et al. |
| 2006/0178631 A1 | 8/2006 | Gillespie et al. |
| 2006/0178642 A1 | 8/2006 | Gillespie et al. |
| 2006/0184119 A1 | 8/2006 | Remde et al. |
| 2006/0184137 A1 | 8/2006 | Reynolds |
| 2006/0189938 A1 | 8/2006 | Hommann et al. |
| 2006/0200093 A1 | 9/2006 | Lopez |
| 2006/0206060 A1 | 9/2006 | Lopez |
| 2006/0224124 A1 | 10/2006 | Scherer |
| 2006/0229572 A1 | 10/2006 | Lopez |
| 2006/0258986 A1 | 11/2006 | Hunter et al. |
| 2006/0258990 A1 | 11/2006 | Weber |
| 2006/0270986 A1 | 11/2006 | Hommann et al. |
| 2007/0027430 A1 | 2/2007 | Hommann |
| 2007/0066939 A1 | 3/2007 | Krulevitch et al. |
| 2007/0078382 A1 | 4/2007 | Hommann et al. |
| 2007/0118094 A1 | 5/2007 | Bingham et al. |
| 2007/0142787 A1 | 6/2007 | Scherer |
| 2007/0156091 A1 | 7/2007 | Fathallah et al. |
| 2007/0156112 A1 | 7/2007 | Walsh |
| 2007/0208296 A1 | 9/2007 | Paproski et al. |
| 2008/0033395 A1 | 2/2008 | Alchas |
| 2008/0172024 A1 | 7/2008 | Yow |
| 2008/0213590 A1 | 9/2008 | Greiner et al. |
| 2008/0269680 A1 | 10/2008 | Ibranyan et al. |
| 2008/0306443 A1 | 12/2008 | Neer et al. |
| 2008/0312602 A1 | 12/2008 | Barrow-Williams et al. |
| 2008/0312606 A1 | 12/2008 | Harrison et al. |
| 2009/0036764 A1 | 2/2009 | Rivas et al. |
| 2009/0054849 A1 | 2/2009 | Burnell et al. |
| 2009/0088688 A1 | 4/2009 | Timothy Donald et al. |
| 2009/0209554 A1 | 8/2009 | Boyd et al. |
| 2009/0234297 A1 | 9/2009 | Jennings |
| 2010/0016793 A1 | 1/2010 | Jennings et al. |
| 2010/0036319 A1 | 2/2010 | Drake et al. |
| 2010/0063444 A1 | 3/2010 | Wikner |
| 2011/0092954 A1 | 4/2011 | Jennings |
| 2011/0098647 A1 | 4/2011 | Jennings |
| 2011/0098655 A1 | 4/2011 | Jennings et al. |
| 2011/0130743 A1 | 6/2011 | Jennings et al. |
| 2011/0282278 A1 | 11/2011 | Stamp et al. |
| 2012/0232491 A1 | 9/2012 | Jennings |
| 2012/0323177 A1 | 12/2012 | Adams et al. |
| 2013/0096512 A1 | 4/2013 | Ekman et al. |
| 2013/0267898 A1 | 10/2013 | Hourmand et al. |
| 2013/0317446 A1 | 11/2013 | Hourmand et al. |
| 2013/0331794 A1 | 12/2013 | Ekman et al. |
| 2013/0338601 A1 | 12/2013 | Cowe |

(56) References Cited

U.S. PATENT DOCUMENTS

| | | |
|---|---|---|
| 2013/0345643 A1 | 12/2013 | Hourmand et al. |
| 2014/0257193 A1 | 9/2014 | Bostrom et al. |

FOREIGN PATENT DOCUMENTS

| | | |
|---|---|---|
| CN | 2059579 U | 7/1990 |
| CN | 1190599 A | 8/1998 |
| CN | 1420794 A | 5/2003 |
| CN | 1541121 A | 10/2004 |
| CN | 1550240 A | 12/2004 |
| CN | 101014379 A | 8/2007 |
| CN | 101068585 A | 11/2007 |
| DE | 902776 C | 1/1954 |
| DE | 229932 A1 | 11/1985 |
| DE | 3604826 A1 | 10/1986 |
| DE | 4428467 A1 | 2/1996 |
| DE | 29513214 U1 | 1/1997 |
| DE | 19603707 A1 | 8/1997 |
| DE | 69506521 T2 | 6/1999 |
| DE | 10137962 A1 | 2/2003 |
| DE | 10207276 A1 | 9/2003 |
| DE | 20311996 U1 | 10/2003 |
| EP | 0111724 B1 | 11/1983 |
| EP | 0096314 A2 | 12/1983 |
| EP | 0144625 A2 | 6/1985 |
| EP | 0240787 A2 | 3/1987 |
| EP | 0338806 A2 | 10/1989 |
| EP | 0515473 B1 | 12/1992 |
| EP | 0518416 A1 | 12/1992 |
| EP | 0331452 A2 | 8/1993 |
| EP | 0585626 A1 | 3/1994 |
| EP | 0389938 B1 | 5/1994 |
| EP | 0516473 B1 | 2/1996 |
| EP | 0482677 B1 | 4/1998 |
| EP | 0602883 B1 | 7/1998 |
| EP | 0857491 A1 | 8/1998 |
| EP | 0824922 B1 | 4/2002 |
| EP | 1260241 A1 | 11/2002 |
| EP | 0824923 B1 | 7/2003 |
| EP | 1228777 B1 | 10/2003 |
| EP | 0991441 B1 | 12/2003 |
| EP | 1166809 B1 | 3/2004 |
| EP | 0666084 B1 | 4/2004 |
| EP | 0941133 B1 | 4/2004 |
| EP | 1124601 B1 | 12/2004 |
| EP | 1364667 B1 | 4/2005 |
| EP | 1208858 B1 | 6/2006 |
| EP | 1755710 A1 | 2/2007 |
| EP | 1586341 B1 | 1/2008 |
| EP | 1932558 A1 | 6/2008 |
| EP | 2023980 A1 | 2/2009 |
| EP | 2129414 A1 | 12/2009 |
| EP | 1755706 B1 | 3/2010 |
| EP | 1928523 B1 | 7/2010 |
| EP | 1518575 B1 | 11/2010 |
| EP | 2468330 A1 | 6/2012 |
| EP | 2340863 B1 | 11/2013 |
| EP | 2620174 B1 | 5/2014 |
| EP | 2675509 B1 | 4/2015 |
| EP | 2705861 B1 | 4/2015 |
| EP | 2414003 B1 | 5/2015 |
| EP | 2464401 B1 | 5/2015 |
| EP | 2493531 B1 | 7/2015 |
| EP | 2705862 B1 | 7/2015 |
| EP | 2588173 B1 | 10/2015 |
| EP | 2470241 B1 | 11/2015 |
| EP | 2768556 B1 | 12/2015 |
| EP | 2355872 B1 | 1/2016 |
| EP | 2720738 B1 | 1/2016 |
| EP | 1412000 B1 | 2/2016 |
| EP | 2671606 B1 | 3/2016 |
| EP | 2760507 B1 | 4/2016 |
| FR | 1014881 A | 8/1952 |
| FR | 1169935 A | 1/1959 |
| FR | 1538565 A | 9/1968 |
| FR | 2506161 A1 | 11/1982 |
| FR | 2629706 A | 10/1989 |
| FR | 2654938 A1 | 5/1991 |
| FR | 2665079 A1 | 1/1992 |
| FR | 2717086 A1 | 9/1995 |
| FR | 2741810 A1 | 6/1997 |
| FR | 2805868 A1 | 9/2001 |
| FR | 2830765 A1 | 4/2003 |
| FR | 2861310 A1 | 4/2005 |
| GB | 143084 | 5/1920 |
| GB | 0412054 | 6/1934 |
| GB | 728248 | 4/1955 |
| GB | 909898 | 11/1962 |
| GB | 1263355 | 2/1972 |
| GB | 1311937 A | 3/1973 |
| GB | 1514725 | 6/1978 |
| GB | 2338033 A | 12/1999 |
| GB | 2388033 A | 11/2003 |
| GB | 2396298 A | 6/2004 |
| GB | 2396816 A | 7/2004 |
| GB | 2397767 A | 8/2004 |
| GB | 2404338 A | 2/2005 |
| GB | 2414398 A | 11/2005 |
| GB | 2414399 A | 11/2005 |
| GB | 2414400 A | 11/2005 |
| GB | 2414401 A | 11/2005 |
| GB | 2414402 A | 11/2005 |
| GB | 2414403 A | 11/2005 |
| GB | 2424835 A | 10/2006 |
| GB | 2424836 A | 10/2006 |
| GB | 2424837 A | 10/2006 |
| GB | 2424838 A | 10/2006 |
| GB | 2425062 A | 10/2006 |
| GB | 2433035 A | 6/2007 |
| GB | 2437922 A | 11/2007 |
| GB | 2438591 A | 12/2007 |
| GB | 2443606 A | 5/2008 |
| GB | 2445090 A | 6/2008 |
| GB | 2446778 A | 8/2008 |
| GB | 2451663 A | 2/2009 |
| GB | 2451665 A | 2/2009 |
| GB | 2452286 A | 3/2009 |
| GB | 2515041 B | 12/2014 |
| JP | 59-115053 A | 7/1984 |
| JP | 2-185261 A | 7/1990 |
| JP | 2-502971 T | 9/1990 |
| JP | H 02-299660 A | 12/1990 |
| JP | 11-501549 T | 2/1992 |
| JP | 5-161712 A | 6/1993 |
| JP | 6-209996 A | 8/1994 |
| JP | 6-508773 T | 10/1994 |
| JP | 6-327770 A | 11/1994 |
| JP | H 07-116224 T | 5/1995 |
| JP | 7-213610 A | 8/1995 |
| JP | 7-222799 A | 8/1995 |
| JP | 8-502180 T | 3/1996 |
| JP | 8-504354 T | 5/1996 |
| JP | 9-225029 A | 9/1997 |
| JP | 10-504474 T | 5/1998 |
| JP | 10-507935 A | 8/1998 |
| JP | 11-503637 T | 3/1999 |
| JP | 11-504536 T | 4/1999 |
| JP | 11-164887 T | 6/1999 |
| JP | 11-512332 T | 10/1999 |
| JP | 2000-126293 A | 5/2000 |
| JP | 2000-510021 T | 8/2000 |
| JP | 2001-046498 A | 2/2001 |
| JP | 2001-212237 A | 8/2001 |
| JP | 2002-500933 T | 1/2002 |
| JP | 2002-502296 A | 1/2002 |
| JP | 2002-095749 A | 4/2002 |
| JP | 2002-513547 T | 5/2002 |
| JP | 2002-526175 A | 8/2002 |
| JP | 2002-528182 T | 9/2002 |
| JP | 2002-532161 T | 10/2002 |
| JP | 2003-511105 T | 3/2003 |
| JP | 2003-532500 T | 11/2003 |
| JP | 2003-533288 A | 11/2003 |
| JP | 2004-533282 T | 11/2004 |

(56) References Cited

FOREIGN PATENT DOCUMENTS

| | | |
|---|---|---|
| JP | 2004-537376 A | 12/2004 |
| JP | 2005-508214 A | 3/2005 |
| JP | 2005-177503 A | 7/2005 |
| JP | 2004-33737 A | 8/2005 |
| JP | 2006-223858 A | 8/2006 |
| JP | 2007-207611 A | 8/2007 |
| JP | 2008-284177 A | 11/2008 |
| NZ | 335985 A | 4/2001 |
| NZ | 573171 A | 11/2010 |
| NZ | 573350 A | 12/2010 |
| WO | WO 87/07843 A1 | 12/1987 |
| WO | WO 88/10129 A1 | 12/1988 |
| WO | WO 98/10129 A1 | 12/1988 |
| WO | WO 92/19296 A | 11/1992 |
| WO | WO 93/02186 A1 | 2/1993 |
| WO | WO 93/21986 A2 | 11/1993 |
| WO | WO 93/23098 A1 | 11/1993 |
| WO | WO 94/04207 A1 | 3/1994 |
| WO | WO 94/07554 A1 | 4/1994 |
| WO | WO 94/11041 | 5/1994 |
| WO | WO 94/13342 A1 | 6/1994 |
| WO | WO 94/21316 A1 | 9/1994 |
| WO | WO 94/22511 A1 | 10/1994 |
| WO | WO 95/04562 A1 | 2/1995 |
| WO | WO 95/29720 A1 | 11/1995 |
| WO | WO 95/31235 A1 | 11/1995 |
| WO | WO 95/35126 A1 | 11/1995 |
| WO | WO 95/35126 A1 | 12/1995 |
| WO | WO 96/30065 A1 | 10/1996 |
| WO | WO 97/10865 A1 | 3/1997 |
| WO | WO 97/13538 A1 | 4/1997 |
| WO | WO 97/48430 A1 | 12/1997 |
| WO | WO 98/11927 A1 | 3/1998 |
| WO | WO 99/03529 A2 | 1/1999 |
| WO | WO 99/10030 A2 | 3/1999 |
| WO | WO 99/22789 A1 | 5/1999 |
| WO | WO 99/37343 A | 7/1999 |
| WO | WO 99/53979 A1 | 10/1999 |
| WO | WO 99/59658 A1 | 11/1999 |
| WO | WO 00/06227 A1 | 2/2000 |
| WO | WO 00/07539 A1 | 2/2000 |
| WO | WO 00/13723 A2 | 3/2000 |
| WO | WO 00/24441 A1 | 5/2000 |
| WO | WO 00/35516 | 6/2000 |
| WO | WO 00/50107 A1 | 8/2000 |
| WO | WO 00/61209 A1 | 10/2000 |
| WO | WO 00/64515 A1 | 11/2000 |
| WO | WO 00/69488 A2 | 11/2000 |
| WO | WO 01/05456 A1 | 1/2001 |
| WO | WO 01/49347 A1 | 7/2001 |
| WO | WO 01/60435 A1 | 8/2001 |
| WO | WO 01/76666 A1 | 10/2001 |
| WO | WO 01/77384 A2 | 10/2001 |
| WO | WO 01/87384 A1 | 11/2001 |
| WO | WO 02/11799 A1 | 2/2002 |
| WO | WO 02/47746 A1 | 6/2002 |
| WO | WO 02/056947 A1 | 7/2002 |
| WO | WO 02/074361 A2 | 9/2002 |
| WO | WO 03/013632 A2 | 2/2003 |
| WO | WO 03/015846 A2 | 2/2003 |
| WO | WO 03/015853 A1 | 2/2003 |
| WO | WO 03/039633 A2 | 5/2003 |
| WO | WO 03/041768 A | 5/2003 |
| WO | WO 03/047663 A2 | 6/2003 |
| WO | WO 03/051434 A2 | 6/2003 |
| WO | WO 03/066141 A1 | 8/2003 |
| WO | WO 03/092771 | 11/2003 |
| WO | WO 03/097133 | 11/2003 |
| WO | WO 03/099358 A2 | 12/2003 |
| WO | WO 2004/007554 A1 | 1/2004 |
| WO | WO 2004/011065 A1 | 2/2004 |
| WO | WO 2004/030732 A2 | 4/2004 |
| WO | WO 2004/035117 A2 | 4/2004 |
| WO | WO 2004/047890 A1 | 6/2004 |
| WO | WO 2004/047891 A1 | 6/2004 |
| WO | WO 2004/047892 A | 6/2004 |
| WO | WO 2004/054644 A1 | 7/2004 |
| WO | WO 2004/054645 A3 | 7/2004 |
| WO | WO 2004/087242 A1 | 10/2004 |
| WO | WO 2004/101025 A2 | 11/2004 |
| WO | WO 2004/108194 A1 | 12/2004 |
| WO | WO 2005/004961 A1 | 1/2005 |
| WO | WO 2005/009515 A1 | 2/2005 |
| WO | WO 2005/023341 A1 | 3/2005 |
| WO | WO 2005/025636 A2 | 3/2005 |
| WO | WO 2005/030301 A1 | 4/2005 |
| WO | WO 2005/035028 A1 | 4/2005 |
| WO | WO 2005/044345 A | 5/2005 |
| WO | WO 2005/044347 A1 | 5/2005 |
| WO | WO 2005/058393 A2 | 6/2005 |
| WO | WO 2005/058396 A1 | 6/2005 |
| WO | WO 2005/070481 A1 | 8/2005 |
| WO | WO 2005/082438 A1 | 9/2005 |
| WO | WO 2005/097238 A3 | 10/2005 |
| WO | WO 2005/105014 A2 | 11/2005 |
| WO | WO 2005/115507 A1 | 12/2005 |
| WO | WO 2005/115508 A1 | 12/2005 |
| WO | WO 2005/115509 A1 | 12/2005 |
| WO | WO 2005/115510 A1 | 12/2005 |
| WO | WO 2005/115512 A1 | 12/2005 |
| WO | WO 2005/115513 A1 | 12/2005 |
| WO | WO 2005/115514 A1 | 12/2005 |
| WO | WO 2005/115516 A1 | 12/2005 |
| WO | WO 2005/120607 A2 | 12/2005 |
| WO | WO 2006/008086 A1 | 1/2006 |
| WO | WO 2006/044236 A2 | 4/2006 |
| WO | WO 2006/050304 A1 | 5/2006 |
| WO | WO 2006/062788 A2 | 6/2006 |
| WO | WO 2006/063015 A2 | 6/2006 |
| WO | WO 2006/063124 A2 | 6/2006 |
| WO | WO 2006/088513 A1 | 8/2006 |
| WO | WO 2006/088630 A2 | 8/2006 |
| WO | WO 2006/099441 A2 | 9/2006 |
| WO | WO 2006/106290 A1 | 10/2006 |
| WO | WO 2006/106291 A1 | 10/2006 |
| WO | WO 2006/106292 A1 | 10/2006 |
| WO | WO 2006/106293 A1 | 10/2006 |
| WO | WO 2006/106294 A | 10/2006 |
| WO | WO 2006/106295 A1 | 10/2006 |
| WO | WO 2006/118616 A1 | 11/2006 |
| WO | WO 2006/129196 A1 | 12/2006 |
| WO | WO 2007/027204 A2 | 3/2007 |
| WO | WO 2007/036676 A1 | 4/2007 |
| WO | WO 2007/047200 A1 | 4/2007 |
| WO | WO 2007/051330 A1 | 5/2007 |
| WO | WO 2007/066152 A | 6/2007 |
| WO | WO 2007/066152 A2 | 6/2007 |
| WO | WO 2007/122193 A1 | 11/2007 |
| WO | WO 2007/129324 A2 | 11/2007 |
| WO | WO 2007/131013 A | 11/2007 |
| WO | WO 2007/138299 A1 | 12/2007 |
| WO | WO 2008/047372 A2 | 4/2008 |
| WO | WO 2008/075033 A | 6/2008 |
| WO | WO 2008/093063 A2 | 8/2008 |
| WO | WO 88/08725 | 11/2008 |
| WO | WO 2010/023303 A1 | 3/2010 |
| WO | WO 2012/000835 A1 | 1/2012 |

OTHER PUBLICATIONS

International Search Report dated May 30, 2006; International Application No. PCT/GB2005/003725.
International Search Report dated Sep. 9, 2005; International Application No. PCT/GB2005/002126.
Australian Search Report dated Dec. 6, 2007; Application No. SG 2006081640.
International Search Report dated Sep. 5, 2005; International Application No. PCT/GB2005/002131.
Austrian Search Report dated Jan. 22, 2006; Application No. 200608166-5.
International Search Report dated Sep. 9, 2005; International Application No. PCT/GB2005/002120.

(56) References Cited

OTHER PUBLICATIONS

European Search Report dated Apr. 23, 2007; Application No. 06077332.2.
International Search Report dated Sep. 5, 2005; International Application No. PCT/GB2005/002105.
Singapore Search Report dated Feb. 26, 2008; Application No. 200608070-9.
International Search Report dated Sep. 5, 2005; International Application No. PCT/GB2005/002116.
International Search Report dated Sep. 5, 2005; International Application No. PCT/GB2005/002128.
International Search Report dated May 23, 2006; International Application No. PCT/GB2006/001017.
International Search Report dated May 29, 2006; International Application No. PCT/GB2006/001018.
International Search Report dated Jun. 2, 2006; International Application No. PCT/GB2006/001030.
International Search Report dated Jun. 1, 2006; International Application No. PCT/GB2006/001029.
International Search Report dated Sep. 9, 2005 International Application No. PCT/GB2005/002135.
International Search Report dated May 30, 2006; International Application No. PCT/GB2006/001031.
International Search Report dated Jun. 27, 2006; International Application No. PCT/GB2006/001023.
International Search Report dated Feb. 27, 2007; International Application No. PCT/1132006/002792.
European Search Report dated Feb. 1, 2006; Application No. 05255298.1.
Great Britain Search Report dated Sep. 22, 2006; Application No. GB0610860.9.
International Search Report dated Aug. 22, 2007; International Application No. PCT/GB2007/001992.
International Search Report dated Sep. 4, 2007; International Application No. PCT/GB2007/002002.
Great Britain Search Report dated Sep. 28, 2006; Application No. GB0610859.1.
International Search Report dated Aug. 22, 2007; International Application No. PCT/GB2007/001973.
International Search Report dated Feb. 26, 2008; International Application No. PCT/GB2007/004335.
International Search Report dated Sep. 13, 2007; International Application No. PCT/GB2007/001999.
International Search Report dated Aug. 28, 2007; International Application No. PCT/GB2007/001969.
International Search Report dated Oct. 10, 2008; International Application No. PCT/GB2008/002578.
Great Britain Search Report dated Nov. 12, 2007; Application No. GB0715460.2.
International Search Report dated Oct. 14, 2008; International Application No. PCT/GB2008/002580.
Great Britain Search Report dated Nov. 12, 2007; Application No. GB0715459.4.
International Search Report dated Nov. 27, 2008; International Application No. PCT/GB2008/002579.
Great Britain Search Report dated Nov. 12, 2007; Application No. GB0715461.0.
International Search Report dated Oct. 10, 2008; International Application No. PCT/GB2008/002573.
Great Britain Search Report dated Nov. 12, 2007; Application No. GB0715456.0.
International Search Report dated Oct. 10, 2008; International Application No. PCT/GB2008/002583.
Great Britain Search Report dated Nov. 12, 2007; Application No. GB0715457.8.
International Search Report dated Sep. 30, 2009; International Application No. PCT/GB2009/001447.
Great Britain Search Report dated Sep. 25, 2008; Application No. GB0811348.2.
International Search Report dated Oct. 2, 2009; International Application No. PCT/GB2009/001448.
Great Britain Search Report dated Sep. 25, 2008; Application No. GB0811346.6.
International Search Report dated Oct. 5, 2009; International Application No. PCT/GB2009/001451.
Great Britain Search Report dated Sep. 25, 2008; Application No. GB0811347.4.
International Search Report dated Oct. 6, 2009; International Application No. PCT/GB2009/001453.
Great Britain Search Report dated Sep. 25, 2008; Application No. GB0811345.8.
International Search Report dated Oct. 5, 2009; International Application No. PCT/GB2009/001445.
Great Britain Search Report dated Sep. 25, 2008; Application No. GB0811349.0.
International Search Report dated Jan. 22, 2010; International Application No. PCT/GB2009/001446.
Great Britain Search Report dated Sep. 25, 2008; Application No. GB0811343.3.
International Search Report dated Jan. 12, 2008; International Application No. PCT/GB2008/002475.
Great Britain Search Report dated Nov. 16, 2007; Application No. GB0716774.5.
European Search Report dated Aug. 3, 2011; Application No. 11170040.
Singapore Search Report dated Mar. 15, 2012; Application No. SG 201007017-5.
European Search Report dated Aug. 3, 2011; Application No. 11170040.7.
European Search Report dated Jul. 20, 2011; Application No. 11163762.5.
Australian Search Report dated Feb. 26, 2008; Application No. SG 200608071-7.
European Search Report dated Feb. 28, 2011; Application No. 10179733.0.
European Search Report dated Mar. 4, 2011; Application No. 10179736.3.
International Search Report dated Sep. 6, 2005; International Application No. PCT/GB2005/002108.
European Search Report dated Jun. 16, 2011; Application No. 11160134.0.
Australian Search Report dated Dec. 11, 2007; Application No. 200608165-7.
European Search Report dated Apr. 17, 2012; International Application No. 12157660.7.
European Search Report dated Apr. 17, 2012; International Application No. 12157661.5.
European Search Report Dated Oct. 16, 2012; International Application No. 12177505.0.
European Search Report dated Aug. 4, 2011; Application No. 11169691.0.
Great Britain Search Report dated Sep. 29, 2006; Application No. GB0610856.7.
Great Britain Search Report dated Sep. 19, 2006; Application No. GB0610861.7.
European Search Report dated Oct. 15, 2013; Application No. 12182553.3.
Great Britain Search Report dated Dec. 9, 2013; Application No. GB1310394.0.
International Search Report dated Sep. 8, 2014; International Application No. PCT/EP2014/062163.
Great Britain Search Report dated Dec. 8, 2013; Application No. GB1310389.0.
International Search Report dated Sep. 8, 2014; International Application No. PCT/EP2014/062166.
Great Britain Search Report dated Dec. 9, 2013; Application No. GB1310402.1.
International Search Report dated Sep. 17, 2014; International Application No. PCT/EP2014/062167.
Great Britain Search Report dated Dec. 9, 2013; Application No. GB1310392.4.

(56) References Cited

OTHER PUBLICATIONS

International Search Report dated Sep. 9, 2014; International Application No. PCT/EP2014/062168.
Great Britain Search Report dated Dec. 10, 2013; Application No. GB1310393.2.
International Search Report dated Sep. 8, 2014; International Application No. PCT/EP2014/062162.
Great Britain Search Report dated Dec. 10, 2013; Application No. GB1310372.6.
International Search Report dated Sep. 16, 2014; International Application No. PCT/EP2014/062160.
European Search Report dated Apr. 28, 2015; Application No. 15153304.9.
International Search Report dated Jan. 29, 2015; International Application No. PCT/EP2014/062167.
International Preliminary Report dated Dec. 15, 2015; International Application No. PCT/EP2014/062163.
International Preliminary Report dated Dec. 15, 2015; International Application No. PCT/EP2014/062166.

* cited by examiner

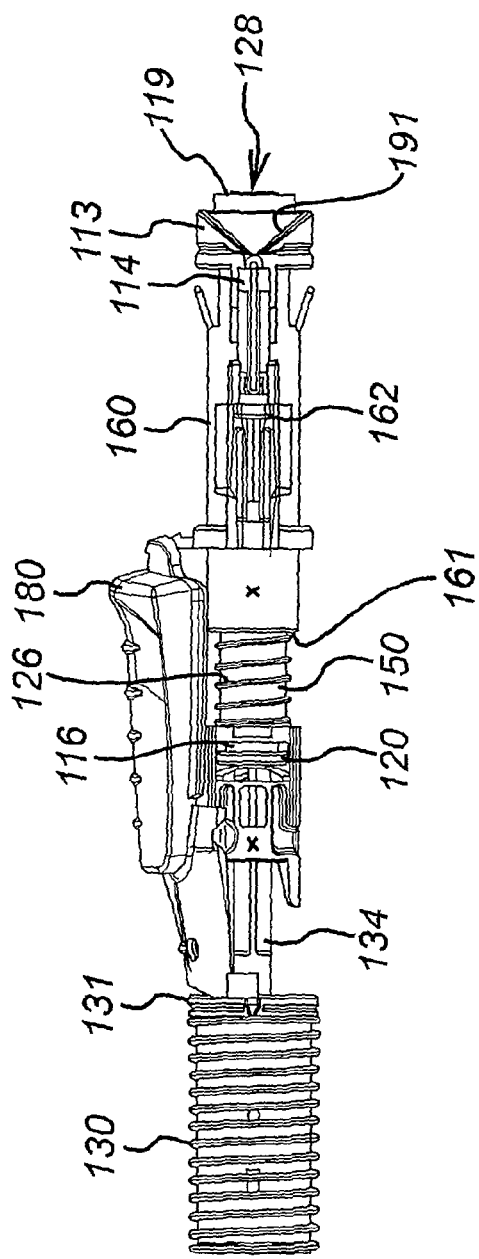
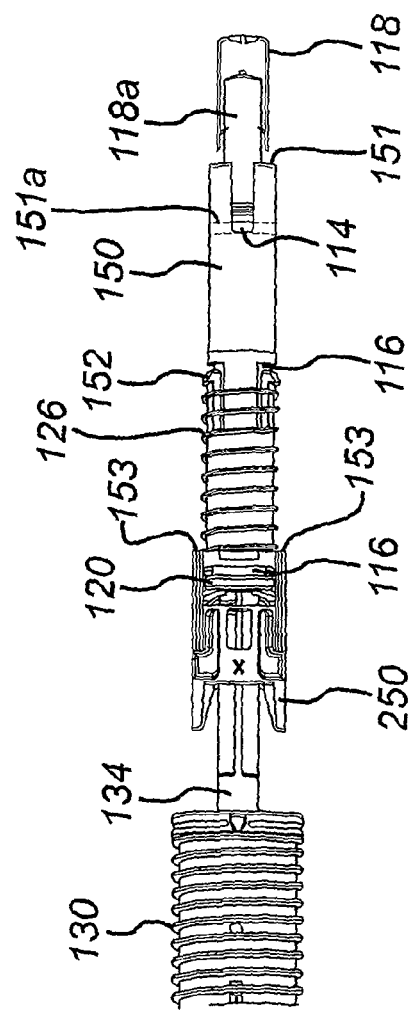
FIG. 2a
FIG. 2b

INJECTION DEVICE

FIELD OF THE INVENTION

The present invention relates to an injection device of the type that receives a syringe, extends it through an exit aperture, discharges its contents and then retracts it automatically.

BACKGROUND OF THE INVENTION

Devices of this general description are shown in WO 95/35126 and EP-A-0 516 473 and tend to employ a drive spring and some form of release mechanism that releases the syringe from the influence of the drive spring once its contents are supposed to have been discharged, to allow it to be retracted by a return spring.

Often, such injection devices are required to work with glass pre-filled syringes that were originally designed for manual use. Such glass syringes have a flange at their base to allow a user to grip the syringe and a needle through which the contents of the syringe can be ejected. Prior to use, the needle is generally covered with a needle shield which may be of plastic or rubber material. The needle shield itself may be contained in a rigid housing which is gripped in a cap on the injection device. Thus, when the cap of the injection device is removed by a user, the needle shield is also removed allowing the device to be operated to extend and expose the needle. The needle shield acts to protect the needle from mechanical damage and maintain its sterility.

In practice, the syringe may not be held rigidly in place within the injection device due, for example, to manufacturing tolerances in the syringe and injection device. In particular, the syringe may be able to move rearwardly in the injection device, i.e. away from the exit aperture. Since the needle shield is gripped in the device cap which is held rigidly in place on a front end of the injection device, if the device is dropped or subjected to adverse external loading, the syringe may move rearwardly so that the needle shield becomes detached from the syringe needle. This is undesirable because the needle is exposed to an environment which may not be sterile. The needle may also become damaged without the protection of the needle shield.

SUMMARY OF THE INVENTION

The injection device of the present invention is designed to deal with the aforementioned problems.

In accordance with a first aspect of the invention, the present invention provides an injection device comprising:
  a housing adapted to receive a syringe having a discharge nozzle at a first end of the syringe, the syringe being movable between a retracted position in which the discharge nozzle is contained within the housing and an extended position in which the discharge nozzle extends from the housing through an exit aperture;
  a drive that acts upon the syringe to advance it from its retracted position to its extended position and discharge its contents through the discharge nozzle; and
  a syringe carrier for carrying the syringe as it is advanced, the syringe carrier having a first end through which the discharge nozzle extends and a second end opposite the first end,
  wherein the syringe carrier is adapted to restrict movement of the syringe relative to the syringe carrier in a direction from the first end of the syringe carrier to the second end of the syringe carrier.

In this way, the syringe and its discharge nozzle can be protected against damage caused by rearward movement within the injection device.

The syringe may comprise a flange at a second end of the syringe opposite the first end of the syringe.

The syringe carrier may comprise, at its second end, means for restricting movement of the syringe relative to the syringe carrier in a direction from the first end of the syringe carrier to the second end of the syringe carrier.

The means for restricting movement may comprise at least one lug on the syringe carrier for preventing movement of the syringe relative to the syringe carrier. The lug may be deformable.

In this way, the syringe can be easily inserted into the syringe carrier during manufacture whilst subsequently being rigidly held at its flange to prevent rearward movement.

Each lug is adapted to be in juxtaposition to the flange on the syringe.

Alternatively, the means for restricting movement comprises at least one damping element.

In this way, movement of the syringe in the syringe carrier is damped and restricted such that the shock of an impact force is not transmitted along the syringe causing damage to the syringe.

The damping element is arranged to bias the syringe in a direction from the second end to the first end of the syringe carrier. Thus, if the impact force is from an end of the injection device, the rearward movement of the syringe can be absorbed by the damping element.

The damping element may comprise resilient biasing means formed from resilient material. In particular, the resilient biasing means could be in the form of an arc of resilient material,
  wherein each end of the arc is attached to the syringe carrier and an outer convex surface of the arc is in juxtaposition with the flange of the syringe.

In this way, the biasing means can be integrally moulded with the syringe carrier for ease of manufacture.

Preferably, the syringe carrier includes a delatch mechanism for releasing the drive from acting on the syringe after the contents of the syringe has been discharged and wherein each end of the arc is attached to the delatch mechanism.

The delatch mechanism may be in the form of an annular portion which is adapted to couple with the drive element in order to disconnect the drive element from the drive.

The discharge nozzle comprises a hypodermic needle and the syringe comprises a removable needle shield on the needle. In this embodiment, the syringe carrier is adapted to prevent rearward movement of the syringe so that the needle shield does not become removed from the syringe when an impact force is applied to the injection device. This prevents the discharge nozzle of the syringe becoming exposed to an non-sterile environment if, for example, the device is dropped onto a hard surface. In addition, the integrity seal of the discharge nozzle connecting to the syringe can be disturbed if rearward movement of the syringe occurs. The present invention overcomes this problem.

BRIEF DESCRIPTION OF THE DRAWINGS

The invention will now be described by way of example with reference to the accompanying drawings, in which:
FIG. 2a shows an enlarged side view of part of the injection device shown in FIG. 1 without its external housing;

FIG. 2b shows an enlarged side view of part of the injection device shown in FIG. 1 without certain internal components of the injection device being shown;

DETAILED DESCRIPTION OF THE INVENTION

Figure 1A:
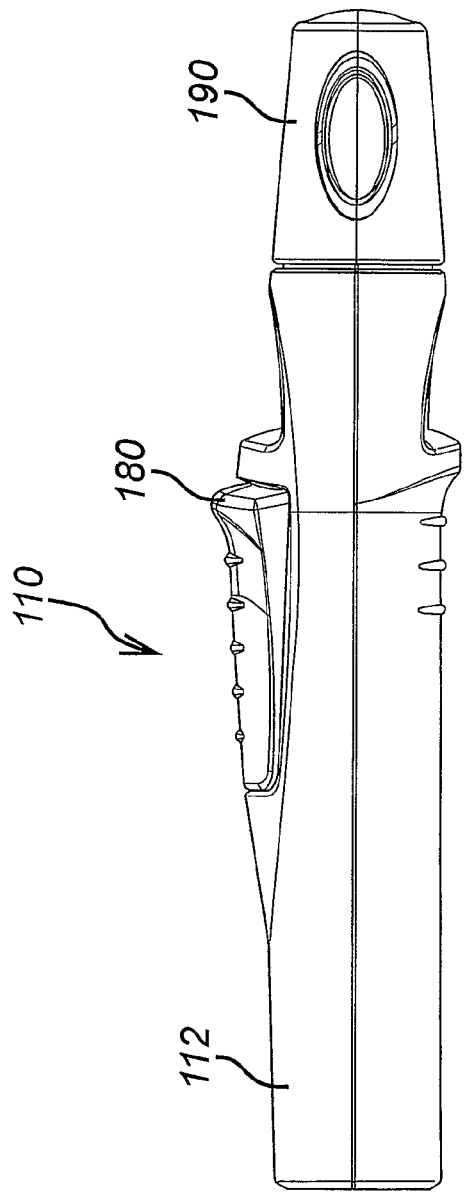
FIGS. 1a and 1b show a side view of an injection device according to the present invention.
Figure 1B:
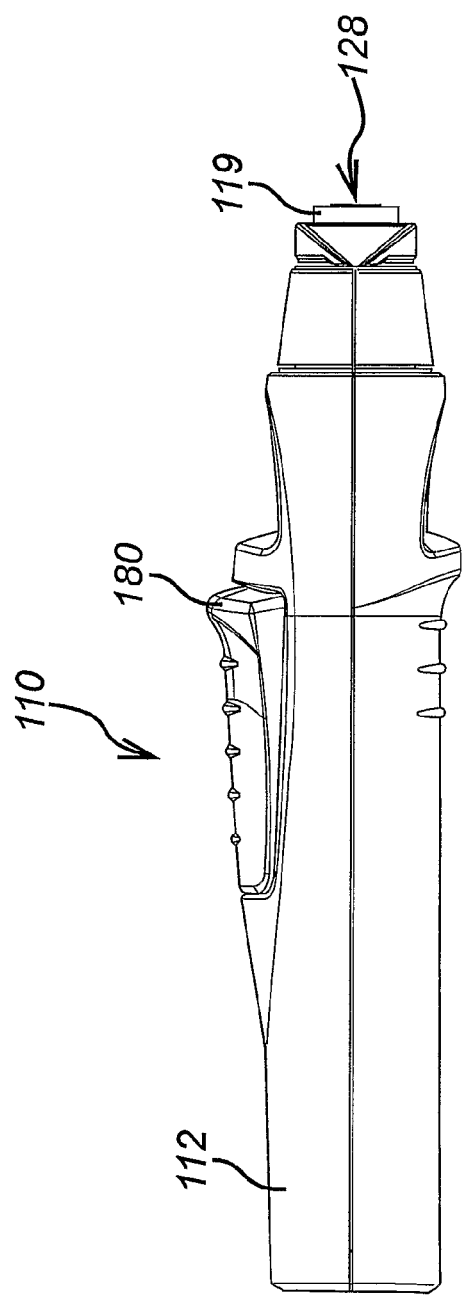

FIGS. 1a and 1b show an injection device 110, having an injection device housing 112. The injection device 110 has a removable cap 190. With the cap 190 removed, as shown in FIG. 2, the end of the housing 112 can be seen to have an exit aperture 128, through which the end of a sleeve 119 can emerge. The injection device 110 also has a trigger 180.

As shown in FIGS. 2a and 2b, the housing 112 contains a hypodermic syringe 114 of conventional type, including a syringe body 116 defining a reservoir and terminating at one end in a hypodermic needle (not shown) and at the other in a flange 120. The hypodermic needle is covered by a needle shield 118. The needle shield 118 is fixed inside the cap 190.

The syringe body 116 is of substantially constant diameter along the length of the reservoir, and is of significantly smaller diameter close to the end of the syringe which terminates in the hypodermic needle. A drive element 134 (syringe piston) acts through the bung of the syringe to discharge the contents of the syringe 114 through the needle 118. This drive element 134 constrains a drug (contained in the syringe) to be administered within the reservoir defined by syringe body 116. Whilst the syringe illustrated is of hypodermic type, this need not necessarily be so. Transcutaneous or ballistic dermal and subcutaneous syringes may also be used with the injection device of the present invention.

The housing 112 comprises a case nose 113 which is integrally formed with a sleeve 160. The sleeve 160 surrounds a syringe carrier 150 which is moveable within the sleeve 160 along its longitudinal axis.

As illustrated, the syringe 114 is housed within the syringe carrier 150. The syringe carrier 150 has a first end 151 and a reduced diameter section 151a. The section 151a of the syringe carrier supports the end of the syringe 114 nearest to the hypodermic needle. The syringe carrier 150 comprises a bearing surface 153 on which an end of a return spring 126 is located. The return spring 126, via the syringe carrier 150 biases the syringe 114 from an extended position in which the needle 118 extends from the aperture 128 in the housing 112 to a retracted position in which the needle 118 is contained within the housing 112.

If the syringe were to fail or break, the syringe carrier 150, which substantially surrounds the syringe 114 along its length, would contain the broken pieces of syringe and reduce the likelihood of them from escaping from the injection device.

The housing 112 also includes a trigger 180, and a drive which here takes the form of a compression drive spring 130. Drive from the drive spring 130 is transmitted via a multi-component drive (118a) to the drive element 134 of the syringe 114 to advance the syringe from its retracted position to its extended position and discharge its contents through the needle 118. The drive accomplishes this task by acting directly on the syringe 114 and the drug in the syringe. Static friction between the drive element 134 and the syringe body 116 initially ensures that both the syringe 114 and bung advance together, until the return spring 126 bottoms out when the bearing surface 153 on the syringe carrier 150 comes up against an opposing bearing surface 161 on the sleeve 160.

The trigger 180 is provided on the housing 112 remote from the exit aperture 128. The trigger, when operated, serves to decouple a drive sleeve 131 on which the drive spring 130 acts from the housing 112, allowing it to move relative to the housing 112 under the influence of the drive spring 130. The operation of the device is then as follows.

The cap 190 can be removed by a user with a twist and pull action or simply by pulling the cap. The exact action required depends on the type of syringe 114 being used. In one embodiment, the syringe 114 will comprise a rigid needle shield 118 containing a rubber boot (not shown) in which the needle is contained. In this embodiment, the needle shield 118 simply needs to be removed by pulling the cap 190 along the longitudinal axis of the device 110. In an alternative embodiment, the syringe 114 comprises a plastic needle shield 118 which is held to the syringe 114 by a frangible connection. In order to break the frangible connection, the cap 190 must be first twisted and then pulled along the longitudinal axis of the device 110. A guiding element 191 on the end cap 113 serves to guide the removal of the cap 190 in the way that is required to remove the needle shield 118.

Since the needle shield 118 is held inside the cap 190, removal of the cap 190, causes the needle shield to be removed, thereby exposing the needle of the syringe 114 within the injection device. At this time, the needle is still enclosed by the housing 112.

Initially, the syringe carrier 150 and syringe 114, are prevented from movement by a resilient latch member 162. By moving the sleeve 119 in a direction into the housing 112, the latch member 162 moves outwards disengaging from the syringe carrier 150. Once the latch member 162 has disengaged from the syringe carrier 150, the syringe 114 and syringe carrier 150 are free to move.

The trigger 180 can then be depressed by a user and the drive spring 130 is released. The drive spring 130 moves the drive sleeve 131, the piston 134 and, by virtue of static friction and hydrostatic forces acting through the drug to be administered, moves the syringe body 114 against the action of the return spring 126. The syringe body 114 moves the syringe carrier 150, which compresses the return spring 126. The hypodermic needle 118 emerges from the exit aperture 128 of the housing 112. This continues until the return spring 126 bottoms out or the syringe body 116 meets some other obstruction (not shown) that retards its motion. Because the static friction between the second drive element 134 and the syringe body 116 and the hydrostatic forces acting through the drug 124 to be administered are not sufficient to resist the full drive force developed by the drive spring 130, at this point the second drive element 134 begins to move within the syringe body 116 and the drug begins to be discharged.

Figure 3A:
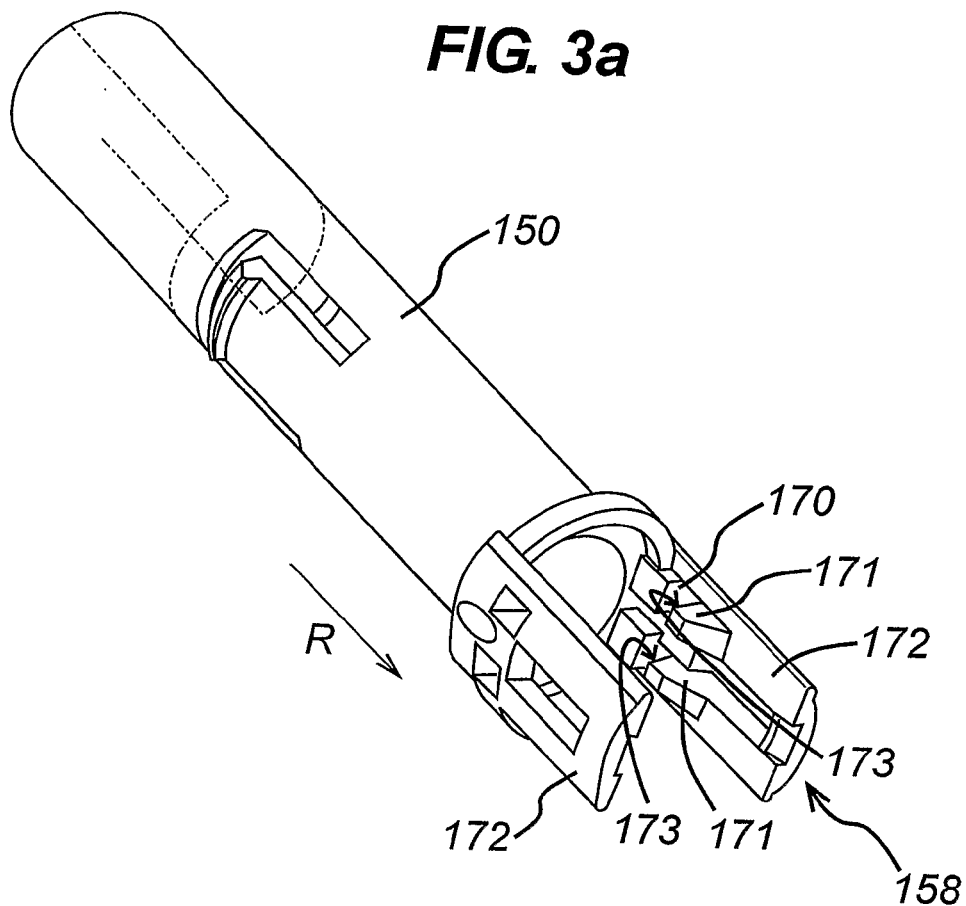
FIGS. 3a and 3b show a perspective view of the syringe carrier in a first embodiment of the invention.
Figure 3B:
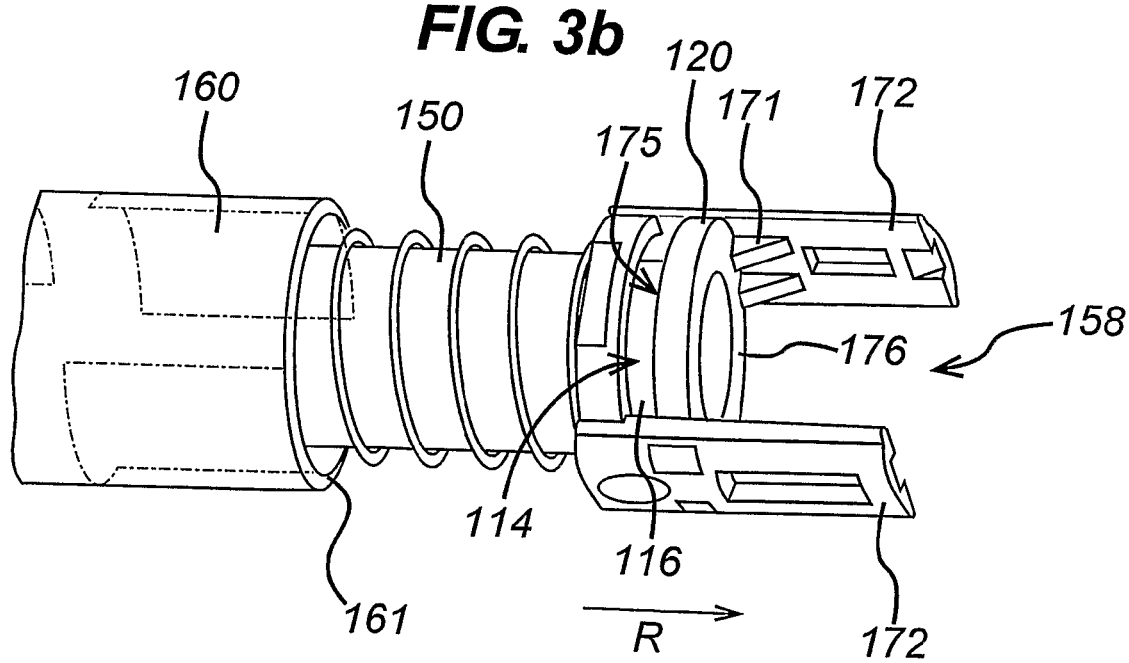

One embodiment of the present invention is depicted in FIGS. 3a and 3b. The syringe carrier is shown with two arms 172 extending from a second end 158 of the syringe carrier 150, opposite its first end 151. As shown in FIG. 3b, the syringe 114 has a flange 120 on its rear end attached to the syringe body 116. An underside 175 of the flange 120 is in juxtaposition with one or more supporting lugs 170 located on the arms 172, wherein each supporting lug provides a supporting interface for the underside 175 of the flange 120 to prevent forward movement of the syringe during device operation.

Each arm 172 also includes means for restricting movement of the syringe relative to the syringe carrier in a direction from the first end of the syringe carrier to the second end of the syringe carrier which are restraining lugs 172 which are dimensioned and shaped with a restraining surface 173 to prevent movement in a rearwards direction R (i.e. movement in a direction from the first end 151 to the second end 158 of the syringe carrier 150) of the syringe 114 relative to the syringe carrier 150. Each restraining surface 173 prevents rearward movement by interfacing with an upper surface 176 of the flange. Following insertion of the syringe 114 into the syringe carrier 150 during manufacture, there may be a nominal separation between the restraining surface 173 and the upper surface 176 of the flange 120. This nominal separation allows some movement of the syringe 114 in a rearwards direction R to buffer the impact of the discharge nozzle as it becomes fully extended during use, thereby reducing pain to a user of the device.

During manufacture of the device 110, the syringe 114 is inserted into the syringe carrier 150 by first inserting its discharge nozzle through the opening at the second end 158 of the syringe carrier 150. The underside 175 of the flange 120 is nominally prevented from passing over the lugs 171. The lugs 171 are sloped on their top surface which means that, as the underside 175 of the flange 120 is pushed over the lugs 171, the arms 172 move apart so that, eventually, the lugs 171 no longer hinder movement of the syringe 114 into the syringe carrier 150 and the restraining surface 173 of the lugs hinders rearward movement of the syringe 114 in the syringe carrier 150.

Figure 4A:
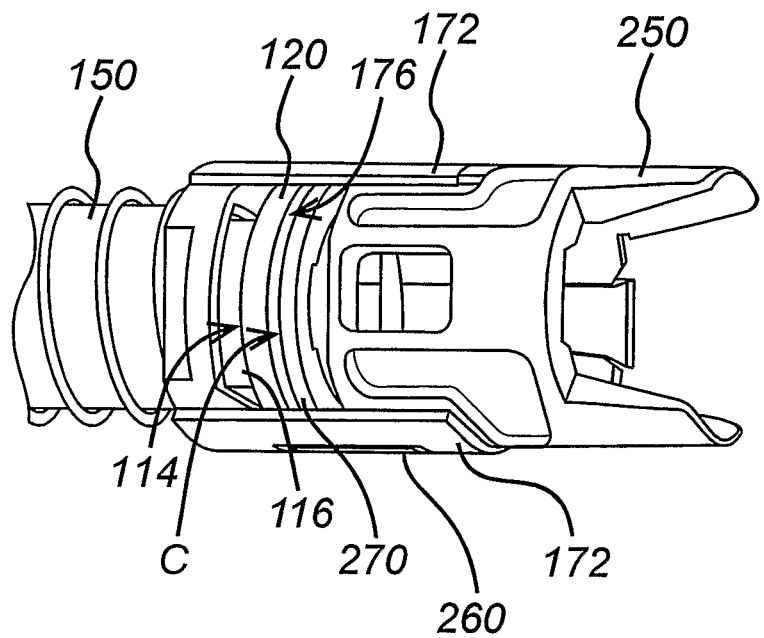
FIGS. 4a and 4b show a perspective view of one embodiment of the syringe carrier in a second embodiment of the invention.
Figure 4B:
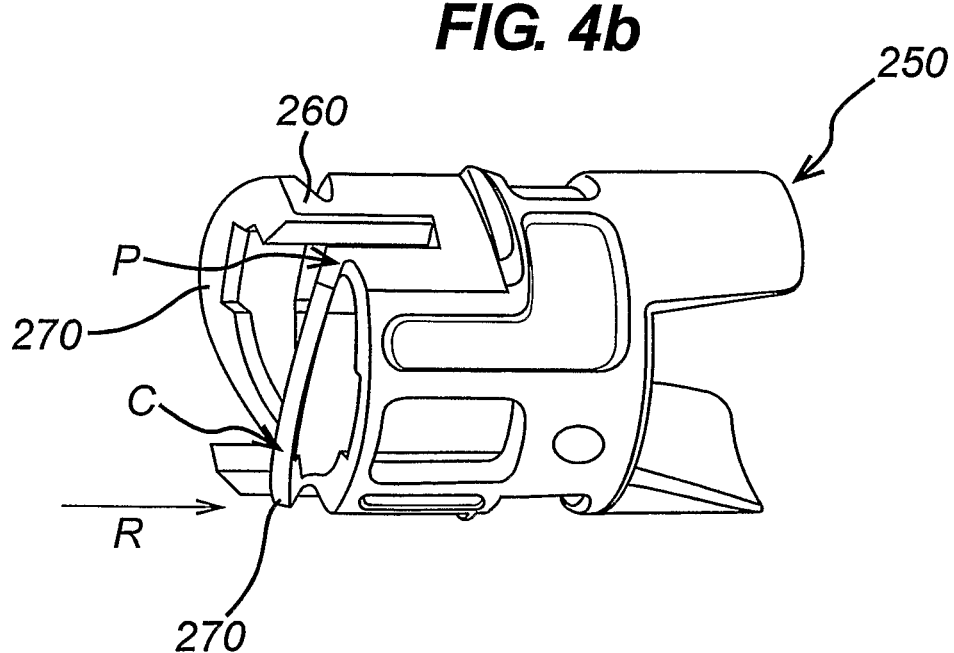

An alternative embodiment of the invention is shown in FIGS. 4a and 4b. In this embodiment, the syringe carrier 150 includes arms 172 and supporting lugs 170 as described above. The syringe carrier also includes a release mechanism 250 that acts to release the drive sleeve 131 from the piston 134 when the drive sleeve 131 moves over the release mechanism 250 when the syringe 114 reaches its extended position. In this way, the force of the drive spring 130 on the syringe 114 is released when it reaches its extended position so that the syringe 114 can then be retracted.

The release mechanism 250 is attached to the arms 172 of the syringe carrier 150 by protrusions 260 which engage with openings (not shown) on the arms 172.

The release mechanism 260 includes two damping elements 270 which are each in the form of an arc of material connected at each end of the arc to the release mechanism 250 at pivot points P. The damping elements 270 are on opposing sides of the release mechanism 250. The damping elements 270 can each resiliently pivot about points P as a result of the resilience of the material and the lever arm formed at the points P. The damping elements 270 can resiliently pivot in a direction R towards the body of the release mechanism 250, providing bias in the opposite direction. In this way, when the release mechanism 250 is rigidly connected via protrusions 260 to the arms 172, following insertion of the syringe 114 during manufacture, a convex section C of each arc is in juxtaposition with the upper surface 176 of the flange 120. Thus, movement of the syringe 114 within the syringe carrier 150 in direction R is damped.

In this way, sudden movement of the syringe 114 caused by an impact force is absorbed by the damping elements 270. Since the damping elements 270 absorb such syringe movement gradually, there is reduced likelihood that the flange 120 can fracture. Moreover, the needle shield 118 remains in place on the discharge nozzle, whilst the integrity seal of the discharge nozzle connecting to the syringe does not get disturbed because sudden rearward movement of the syringe 114 is damped.

It will of course be understood that the present invention has been described above purely by way of example and modifications of detail can be made within the scope of the invention.

The invention claimed is:

1. An injection device comprising:
   a housing having a syringe with a syringe body having a discharge nozzle at a first end of the syringe body, the syringe body being movable between a retracted position in which the discharge nozzle is contained within the housing and an extended position in which the discharge nozzle extends from the housing through an exit aperture, wherein the syringe body comprises a flange at a second end of the syringe body opposite the first end of the syringe body;
   a drive element comprising a syringe piston, wherein the syringe piston acts directly upon the syringe body to advance it from its retracted position to its extended position and discharge its contents through the discharge nozzle; and
   a syringe carrier for carrying the syringe body as it is advanced, the syringe carrier having a first end through which the discharge nozzle extends and a second end opposite the first end,
   wherein the syringe carrier comprises, at its second end, at least one damping element for restricting movement of the syringe body relative to the syringe carrier in a direction from the first end of the syringe carrier to the second end of the syringe carrier whilst allowing some movement of the syringe body, relative to the syringe carrier, in the direction from the first end of the syringe carrier to the second end of the syringe carrier,
   wherein the damping element is arranged to bias the syringe in a direction from the second end to the first end of the syringe carrier, and wherein
   the damping element comprises biasing means formed from resilient material, and
   the biasing means is in the form of an arc of resilient material, wherein
   each end of the arc is attached to the syringe carrier and an outer convex surface of the arc is in juxtaposition with the flange of the syringe.

2. The injection device of claim 1, further comprising a drive which acts on the syringe via the drive element, wherein the syringe carrier includes a delatch mechanism for releasing the drive from acting on the syringe after the contents of the syringe has been discharged and wherein the damping element is located on the delatch mechanism.

3. The injection device of claim 2, wherein the delatch mechanism is in the form of an annular portion which is adapted to couple with the drive element in order to disconnect the drive element from the drive.

4. The injection device of claim 1, wherein the discharge nozzle comprises a hypodermic needle and the syringe comprises a removable needle shield on the needle.

* * * * *